US012633166B1

(12) United States Patent
Zhao et al.

(10) Patent No.: US 12,633,166 B1
(45) Date of Patent: May 19, 2026

(54) SYSTEM FOR BIOMETRIC USER LIVENESS ASSESSMENT

(71) Applicant: AMAZON TECHNOLOGIES, INC., Seattle, WA (US)

(72) Inventors: Rui Zhao, Bellevue, WA (US); Charles Joseph Tucker Peach, Kirkland, WA (US); Baomin Wang, State College, PA (US); Evan Perillo, Woodinville, WA (US); Abhinav Kashyap, Redmond, WA (US); Manoj Aggarwal, Seattle, WA (US); Gerard Guy Medioni, Los Angeles, CA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 281 days.

(21) Appl. No.: 18/469,703

(22) Filed: Sep. 19, 2023

(51) Int. Cl.

| | |
|---|---|
| ***G06V 40/40*** | (2022.01) |
| ***A61B 5/117*** | (2016.01) |
| ***G06T 7/70*** | (2017.01) |
| ***G06V 10/143*** | (2022.01) |
| ***G06V 40/10*** | (2022.01) |
| ***H04N 23/11*** | (2023.01) |
| ***H04N 23/56*** | (2023.01) |

(52) U.S. Cl.
CPC .............. *G06V 40/45* (2022.01); *A61B 5/117* (2013.01); *G06T 7/70* (2017.01); *G06V 10/143* (2022.01); *G06V 40/11* (2022.01); *H04N 23/11* (2023.01); *H04N 23/56* (2023.01); *G06T 2207/10152* (2013.01); *G06T 2207/30196* (2013.01)

(58) Field of Classification Search
CPC ...................................................... G06V 40/45
USPC ........................................................... 348/77
See application file for complete search history.

(56) References Cited

U.S. PATENT DOCUMENTS

| | | | | |
|---|---|---|---|---|
| 7,995,808 | B2 * | 8/2011 | Rowe | G06V 40/1312 382/124 |
| 8,058,616 | B2 * | 11/2011 | Schwaneberg | G06V 40/1394 250/338.4 |
| 9,996,726 | B2 * | 6/2018 | Chen | G06V 40/1347 |
| 10,452,894 | B2 * | 10/2019 | Zhang | G06V 40/166 |
| 12,106,607 | B2 * | 10/2024 | Boic | G06V 40/166 |
| 12,277,794 | B1 * | 4/2025 | Wang | G06V 10/143 |
| 2008/0298649 | A1 * | 12/2008 | Ennis | G06V 40/45 382/125 |
| 2010/0246902 | A1 * | 9/2010 | Rowe | G07D 7/121 382/115 |

(Continued)

*Primary Examiner* — Leron Beck
(74) *Attorney, Agent, or Firm* — Lindauer Law, PLLC

(57) ABSTRACT

An input device includes multiwavelength reflectance spectroscopic (MWRS) hardware having a first field of view (FOV) and one or more cameras with respective FOVs that differ from the first FOV. The one or more cameras are used to obtain image data. When a hand is determined to be at a specified position within the first FOV and in a specified pose, the MWRS hardware is operated to obtain intensity data. The intensity data is processed to determine liveness data indicative of whether an object in the first FOV is an actual user or an artifact. The image data obtained within a specified time interval relative to the acquisition of the liveness data indicative of an actual user may then be processed to identify the user. Additional assessments may be performed to validate the image data, such as confirming continuity between acquisition of the liveness data and the image data obtained.

20 Claims, 7 Drawing Sheets

(56) References Cited

U.S. PATENT DOCUMENTS

| | | | | |
|---|---|---|---|---|
| 2017/0337412 | A1* | 11/2017 | Bhat | G06V 40/1318 |
| 2018/0239944 | A1* | 8/2018 | Ohno | A61B 5/0075 |
| 2018/0239955 | A1* | 8/2018 | Rodriguez | G06V 40/171 |
| 2019/0026451 | A1* | 1/2019 | Venkatesan | G06V 40/1312 |
| 2019/0302963 | A1* | 10/2019 | Harrison | G06V 40/28 |
| 2020/0250874 | A1* | 8/2020 | Assouline | G06N 3/08 |
| 2022/0121869 | A1* | 4/2022 | Miura | G06T 7/11 |
| 2022/0343542 | A1* | 10/2022 | Bae | H04N 13/332 |

* cited by examiner

FIG. 5B
From FIG. 5A
500 (CONTINUED)
DETERMINE SECOND DISTANCE DATA 552
ACQUIRE SECOND INPUT IMAGE DATA AT A THIRD TIME 554
SECOND DISTANCE DATA WITHIN THRESHOLD DISTANCE? 556
NO (DISCONTINUITY)
YES
HAND DETECTED? 580
NO (DISCONTINUITY)
YES
DETERMINE SECOND POSITION DATA 582
SECOND POSITION DATA WITHIN THRESHOLD POSITION? 584
NO (DISCONTINUITY)
YES
DETERMINE SECOND POSE DATA 586
SECOND POSE DATA WITHIN THRESHOLD POSE? 588
NO (DISCONTINUITY)
YES
DETERMINE THE SECOND INPUT IMAGE DATA IS INVALID 558
OPERATE THE LIGHT SOURCE(S) AND THE SPECTROSCOPY SENSOR TO DETERMINE INTENSITY DATA AT A FOURTH TIME 560
DETERMINE SECOND LIVENESS DATA 562
DETERMINE AT LEAST A PORTION OF ONE OR MORE OF THE FIRST INPUT IMAGE DATA OR THE SECOND INPUT IMAGE DATA IS VALID BIOMETRIC INPUT IMAGE DATA 590
DETERMINE REPRESENTATION DATA BASED ON THE VALID BIOMETRIC INPUT DATA 592

INPUT DEVICE 104

POWER SUPPLY 602

PROCESSOR(S)
604

CLOCK
606

COMMUNICATION
INTERFACE(S) 608

I/O INTERFACE(S) 610

NETWORK INTERFACE(S)
612

TAMPER DETECTION
CIRCUITRY
660

I/O DEVICE(S) 614

INPUT DEVICE(S) 616

VISIBLE LIGHT
CAMERA 108(1)

SPECTROSCOPY
SENSOR 170

TOUCH SENSOR
616(3)

IR CAMERA(S)
108(2)

CARD READER
616(1)

MICROPHONE
616(4)

DISTANCE
SENSOR 144

SWITCH 616(2)

...

OUTPUT DEVICE(S) 618

VISIBLE LIGHT
SOURCE(S) 140

IR LIGHT
SOURCE(S) 142

DISPLAY 650

SPEAKER 652

...

MEMORY 620

OPERATING SYSTEM MODULE 622

COMMUNICATION MODULE 626

LIVENESS TRIGGER MODULE 148

IMAGE ANALYSIS MODULE 152

DEVICE CONTROL MODULE 162

MULTIWAVELENGTH REFLECTANCE
SPECTROSCOPY ANALYSIS MODULE
174

VALIDITY MODULE 180

REPRESENTATION NETWORK
MODULE(S) 420

...

OTHER MODULE(S) 630

DATA STORE 624

OPERATING PARAMETERS 632

SENSOR DATA 634

CARD DATA 636

DEVICE IDENTIFICATION DATA 638

LIVENESS DATA 176

INPUT DATA 642

REPRESENTATION DATA 436

OUTPUT DATA 644

...

OTHER DATA 646

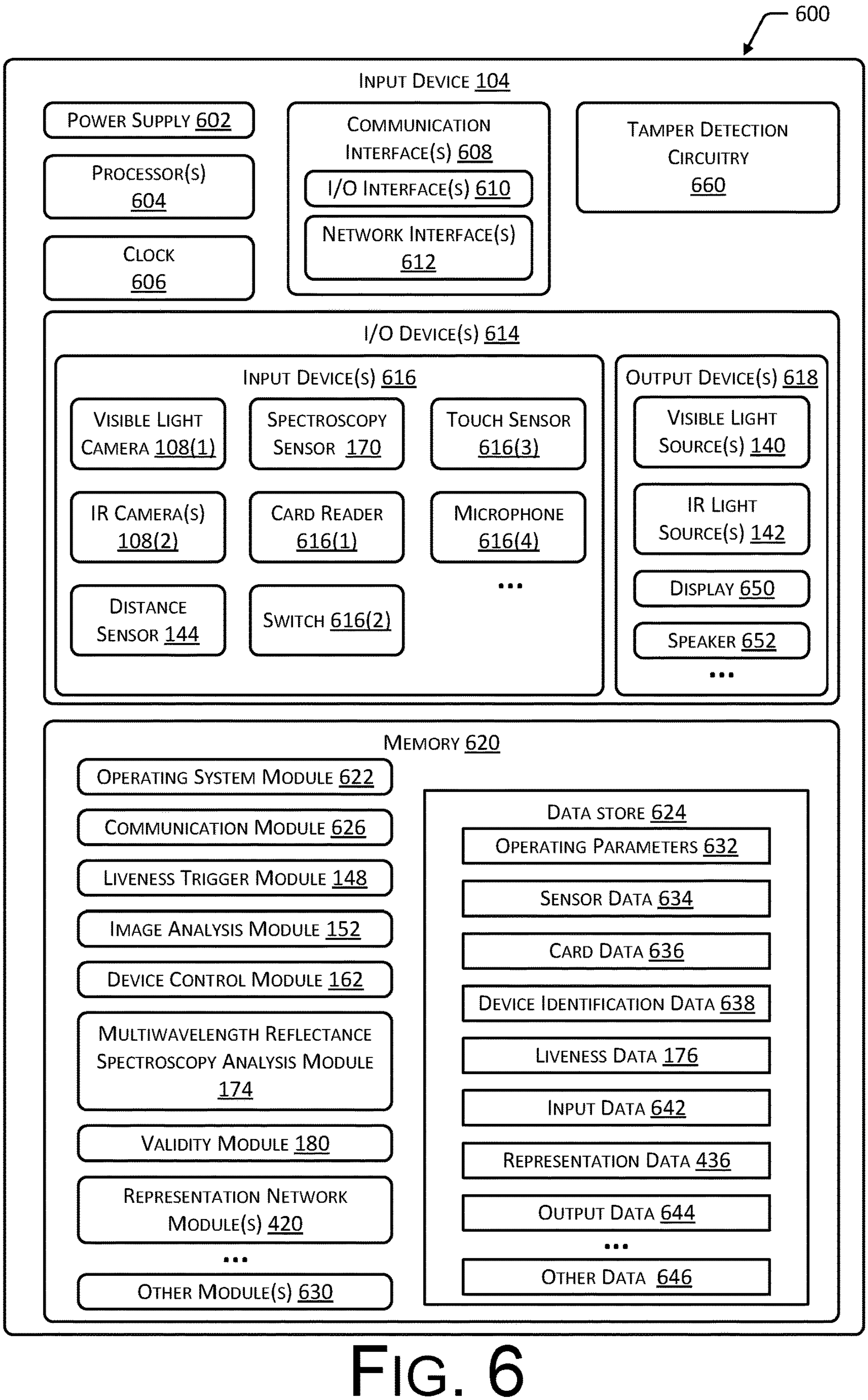

FIG. 6

SYSTEM FOR BIOMETRIC USER LIVENESS ASSESSMENT

BACKGROUND

Facilities such as stores, libraries, hospitals, offices, apartments, and so forth, may need the ability to identify users at the facility or acquire other input.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features. The figures are not necessarily drawn to scale, and in some figures, the proportions or other aspects may be exaggerated to facilitate comprehension of particular aspects.

FIG. 6 is a block diagram of the input device, according to some implementations.

Figure 1:
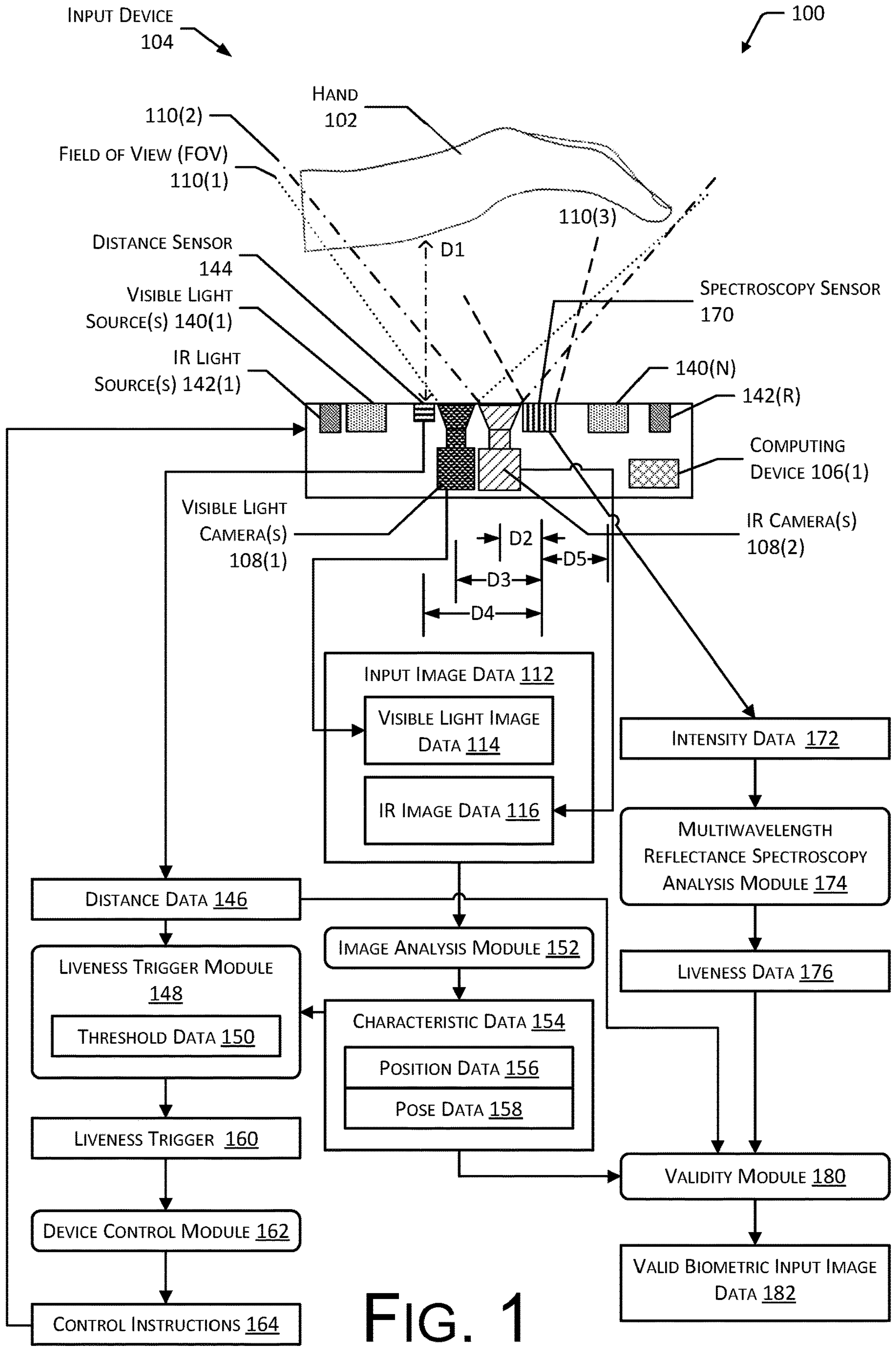
FIG. 1 illustrates an input device to provide biometric input data deemed valid based at least in part on multiwavelength reflectance spectroscopy, according to some implementations.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

DETAILED DESCRIPTION

Accurate and fast acquisition of input by an input device may be used in a variety of ways including determining if physical access is permitted, determining a payment method to be used, and so forth. The input device may acquire biometric input.

In one implementation, the biometric input may be used to facilitate payment for goods or services. For example, an input device may be used at a point-of-sale (POS). Biometric input may be obtained and used to determine an identity of a user. The identity of the user may then be associated with a payment method, such as an account, previously stored bank or credit card account, and so forth.

In other implementations, based on this identity, other actions may be performed. For example, entrance to an office, residence, warehouse, transportation facility, or other location may be responsive to a user presenting biometric input at an entry portal. In another example, the biometric input may be used to provide information as to the particular user who agreed to a contract, accepted a delivery, and so forth.

Traditional systems for identifying users suffer from several significant drawbacks including susceptibility to presentation attacks, lack of speed, inaccuracy, and operational limitations. Biometric identification systems identify users based on characteristics of the particular individual that is difficult or impossible to copy or be transferred. Operation of traditional biometric identification systems introduce operational problems such as slow data acquisition, limited resolution, increased wear in heavy-use environments, and so forth. For example, traditional palm-based biometric identification systems require physical contact between the user's hand and a scanning device. This physical contact may be deemed unsanitary and may be difficult to accomplish for some users. These traditional systems are also susceptible to presentation attacks involving an artifact that attempts to produce biometric input. For example, a presentation attack may attempt to use an artifact comprising a plastic model of a hand to pose as an enrolled user.

Described in this disclosure is an input device that, when triggered by one or more characteristics satisfying specified conditions, performs a liveness detection process that uses multiwavelength reflectance spectroscopy to determine liveness data indicative of whether an object within a field of view (FOV) is a live user or an artifact. The one or more characteristics may be determined based on data from one or more sensors. These sensors may include one or more of a distance sensor, one or more cameras, multiwavelength reflectance spectroscopy (MWRS) hardware, or other sensors.

The distance sensor may determine presence of an object. The distance sensor may comprise an optical time-of-flight sensor. When the distance sensor detects presence of an object, one or more operations may be performed by the device. For example, when an object is detected, the input device may begin operating one or more portions of the input device such as light sources, other sensors, and so forth.

The input device may include one or more light sources. The light sources may be used to provide illumination for the one or more cameras, the MWRS hardware, and so forth. A light emitting diode (LED), quantum dot, laser, or other device may be used to emit light at one or more wavelengths. For example, some LEDs may emit visible light at one or more wavelengths while other LEDs may emit infrared light at one or more wavelengths. In some implementations the light sources may be used to provide output to the user.

The one or more cameras may include one or more of a visible light camera sensitive to visible light, or an infrared camera sensitive to infrared light. Each camera may have a respective FOV. For example, the visible light camera may have a first FOV while the infrared camera has a second FOV. The camera(s) may acquire input image data during operation.

The input image data acquired by the visible light camera may include images of the surface of the hand. For example, a set of images acquired by the visible light camera may depict external characteristics such as lines and creases in the user's palm and fingers.

The input image data acquired by the infrared camera may include images of the surface of the hand, subcutaneous features, or both. In one implementation, polarized infrared light sources in the input device may be activated at different times to provide illumination while an infrared camera in the device that is sensitive to infrared light acquires images at the different times. Objects within the infrared camera's FOV may be illuminated by infrared light having different polarizations at different times. For example, a first set of one or more images may be obtained that use infrared light with a first polarization and a second set of one or more images that use infrared light with a second polarization may be obtained. The infrared camera may include a polarizer with the first polarization. The first set of images depict external characteristics, such as lines and creases in the user's palm while the second set of images depict internal anatomical structures, such as veins, bones, soft tissue, or other structures beneath the epidermis of the skin.

The MWRS hardware may comprise one or more sensors that are sensitive to a plurality of wavelengths. The spectroscopy sensor(s) of the MWRS may have a third FOV that differs from that of the cameras. For example, the relative placement with respect to the input device and optics may result in the difference in fields of view. The third FOV may overlap one or more of the first FOV or the second FOV.

In one implementation the spectroscopy sensor of the MWRS may comprise a photodetector used to acquire intensity data and may utilize the light sources to provide a timed sequence of illumination at specific wavelengths. For example, at a first time the light sources may be operated to illuminate the third FOV with light having a wavelength of 415 nanometers (nm) and first intensity data is acquired using the photodetector, at a second time the light sources are operated to illuminate the third FOV with light having a wavelength of 445 nm and second intensity data is acquired using the photodetector, and so forth.

In another implementation the spectroscopy sensor of the MWRS may comprise a multispectral sensor comprising a plurality of photodetectors, each with a respective filter that passes light with a particular wavelength. The multispectral sensor may be used to acquire intensity data with respect to a plurality of wavelengths during a single sample interval. For example, at a first time the light sources may be operated to illuminate the third FOV with light having a wavelength of 415 nm and light having a wavelength of 445 nm. The multispectral sensor may be used to acquire first intensity data associated with 415 nm and second intensity data associated with 445 nm.

Images acquired from one or more of the cameras of the input device are used to acquire images of an object within the respective camera FOV. These images are processed to determine one or more characteristics. In one implementation these characteristics may include a hand position and hand pose. The hand position may be the apparent position of the user's hand, or a portion thereof, within the image. The hand pose may be indicative of the orientation of the hand and articulation of joints.

If the hand position satisfies a specified position threshold and the hand pose satisfies a specified pose threshold, the multiwavelength reflectance spectroscopy (MWRS) hardware may be triggered to acquire intensity data. For example, if the hand as depicted in the image is within a specific location, such as having the palm center within a specified region of the image, and if the hand pose is such that the palm is facing the camera and the hand is held with the fingers flat and outstretched, then the MWRS hardware may be triggered to operate and determine intensity data. The intensity data may then be processed to determine liveness data.

Responsive to the liveness data, the device may perform one or more operations, such as processing acquired image input data. For example, input image data that is associated with liveness data indicative of an actual hand may be processed to determine representation data. The representation data may be indicative of features in the images. In one implementation the input image data may be processed, at least in part, locally on the device. In another implementation the input image data, or data based on the input image data, may be encrypted and transmitted to a server for processing to determine identity, payment account information, authorization to pass through a portal, and so forth.

By determining the liveness data as described, vulnerability from presentation attacks is substantially reduced. The system provides a high degree of assurance that the input is associated with an actual person, and not a constructed artifact. In the event an artifact is determined to be present, mitigating actions may be taken. For example, the input device may be disabled for a period of time, an alarm notification may be issued, data in internal memory may be erased, one or more anti-tampering functions may be performed, and so forth.

By selectively triggering the MWRS several advantages may be realized. In some implementations, the MWRS process may produce an effect that is perceptible to some users. For example, the MWRS process may result in what the user perceives as a transient change in the illumination provided by the input device. Users may find this disconcerting, and so minimizing the MWRS process may result in an improved user experience.

Selective triggering may reduce the number of times the MWRS process is performed, and may change the relative timing of the MWRS process. These minimize the opportunity for an adversary to analyze or attempt to circumvent the MWRS process.

Selective triggering and the subsequent determination of liveness data may also reduce data storage, bandwidth, and data processing requirements, improving overall system efficiency. For example, images associated with liveness data indicating an actual hand may be processed, while images associated with liveness data indicative of an artifact may be discarded.

The input device utilizing the selective triggering is compact, allowing easy integration with existing or new systems. The input device facilitates rapid acquisition of input in a variety of situations. The input device is easily deployed, and different implementations may be used as a portable device, placed on a supporting structure, affixed to a stand, integrated with another device, and so forth. By assessing the user and using the biometric input acquired by the device, a computer system is able to determine the physical presence of a particular user at the particular input device at a particular time. This information may be used to authorize payment of a transaction, gain entry to a secured area, sign a contract, and so forth.

Illustrative System

FIG. 1 illustrates at 100 an input device 104 to provide biometric input data deemed valid based at least in part on multiwavelength reflectance spectroscopy (MWRS), according to some implementations. The biometric input data deemed valid may be used for biometric identification that asserts an identity of a user at the input device 104. However, the input device and techniques described herein may be used in other situations.

A hand 102 of a user is depicted positioned above an input device 104. The input device 104 may include a computing device 106(1) and one or more cameras 108. Each camera 108 has a field of view (FOV) 110. During operation of the input device 104, the camera 108 acquires images of an object in the respective FOV 110, such as the hand 102, and provides as output input image data 112.

The input device 104 includes one or more light sources to emit light during operation. For example, the light sources may comprise light emitting diodes (LEDs), quantum dots, electroluminescent devices, fluorescent devices, lamps, vertical-cavity surface-emitting lasers (VCSELs), and so forth. The light sources may, during operation, provide illumination of the object in one or more of the FOVs 110(1)-(F). The one or more light sources may include one or more visible light sources 140(1)-(N) or infrared (IR) light sources 142 (1)-(R). During operation, the light sources emit light at one or more wavelengths. For example, a visible light source 140 may emit one or more wavelengths of visible light. In another example, an IR light source 142 may emit one or more wavelengths of infrared light.

The input device 104 may comprise one or more cameras 108. In the implementation depicted, the input device 104 comprises two cameras: a visible light camera 108(1) and an infrared camera 108(2). The visible light camera 108(1) is sensitive to visible light. In some implementations the visible light camera 108(1) may provide as output monochrome images or color images such as red-green-blue (RGB) images. The visible light camera 108(1) has a first FOV 110(1). The visible light camera 108(1) acquires and provides as output visible light image data 114.

The IR camera 108(2) is sensitive to infrared light. In some implementations the IR camera 108(2) may provide as output monochrome images or multiwavelength images. The IR camera 108(2) has a second FOV 110(2). The IR camera 108(2) acquires and provides as output IR image data 116. In some implementations, the IR camera 108(2) may provide images using different modalities.

In one implementation, the input device 104 is configured to acquire images of the hand 102 that are illuminated using IR light source(s) 142 that have one or more particular polarizations, with different illumination patterns, and so forth. For example, during operation the user may present their hand 102 to the input device 104. The IR image data 116 may comprise images acquired using different combinations of polarized light provided by the IR light sources 142.

Depending upon the polarization used, the images produced by the IR camera 108(2) may be of first modality features or second modality features. The first modality may utilize images in which the hand 102 is illuminated with infrared light having a first polarization and obtained by the IR camera 108(2) with a polarizer passing light to the IR camera 108(2) that also has the first polarization. First modality features may comprise features that are close to, or on, a surface of the hand 102 of the user. For example, the first modality features may include surface features such as creases, wrinkles, scars, dermal papillae ridges, and so forth in at least the epidermis of the hand 102. Images acquired using the first modality may be associated with one or more surface features.

The second modality may utilize images in which the hand 102 is illuminated with infrared light having a second polarization and obtained by the IR camera 108(2) with the polarizer passing light to the IR camera 108(2) having the first polarization. Second modality features comprise those features that are below the epidermis. For example, the second modality features may include subcutaneous anatomical structures such as veins, bones, soft tissue, and so forth. Some features may be visible in both first modality and second modality images. For example, a crease in the palm may include first modality features on the surface as well as deeper second modality features within the palm. Images acquired using the second modality may be associated with one or more subcutaneous features.

Separate images of the first and second modalities may be acquired using different combinations of polarized light provided by the IR light sources 142. In this illustration, the IR image data 116 in the input image data 112 may comprise first modality image data and second modality image data. The first modality image data and the second modality image data of the same object may be acquired in rapid succession with respect to one another. For example, the IR camera 108(2) may operate at 60 frames per second and acquire the first modality image data in a first frame and the second modality image data in a second frame.

In some implementations, other camera configurations may be used. For example, a single camera may be used that is sensitive to visible light and infrared light. In another example, a camera may be sensitive to ultraviolet light.

The input device 104 may comprise a distance sensor 144 that during operation determines distance data 146 that is indicative of a distance to an object, such as D1 shown in FIG. 1. The distance sensor 144 may comprise an optical time-of-flight (TOF) sensor. The optical TOF sensor may include a light source, or may use one or more of the light sources of the input device, to emit a strobe or pulse of light and detect a reflection of at least a portion of that pulse using a detector. For example, the distance sensor 144 may include an infrared (IR) strobe that emits a pulse of light and an infrared photodetector to detect a reflection. Based on the time difference between the emission and the detection and known propagation of speed of light, the distance to an object may be calculated. In other implementations the distance sensor may comprise an ultrasonic device, radar device, capacitive distance sensor, capacitive proximity sensor, inductive distance sensor, inductive proximity sensor, and so forth. For example, the distance sensor may comprise an ultrasonic transducer that emits ultrasonic pulses and a microphone or other transducer that detects reflections of those ultrasonic pulses.

In some implementations, the distance data 146 may be used to transition the device from one operating mode to another. For example, the input device 104 may be in a low power or "sleep" mode until an object is detected at less than a threshold distance. Responsive to this detection, the input device 104 may transition to a high-power or "wake" mode. While in the high-power mode, the input device 104 may operate one or more devices, such as the light sources, cameras 108, and so forth.

The input device 104 includes multiwavelength reflectance spectroscopy (MWRS) hardware that is used to determine intensity data 172 of a plurality of wavelengths. The MWRS hardware includes a spectroscopy sensor 170 and may utilize other devices, such as the one or more light sources. For example, during operation one or more of the light sources are operated to emit light and the spectroscopy sensor 170 is used to determine intensity data 172 indicative of the intensity of reflected light. The intensity data 172 may then be processed by an MWRS analysis module 174 to determine liveness data 176.

Distances between various devices in the implementation are also depicted. A distance D2 between the spectroscopy sensor 170 and the infrared camera 108(2) is shown. A distance D3 between the spectroscopy sensor 170 and the visible light camera 108(1) is shown. A distance D4 between the spectroscopy sensor 170 and the distance sensor 144 is shown.

The spectroscopy sensor 170 and a nearest light source for at least a particular wavelength the spectroscopy sensor 170 is sensitive to may be arranged such that there is a distance D5 between them. The distance D5 may increase the difficulty associated with providing false data to the input device 104. The distance D5 increases the volume of the third FOV 110(3). For example, the spectroscopy sensor 170 may be mounted at least one centimeter from any of the visible light sources 140 that are used in conjunction with the spectroscopy sensor 170. In this example, an object within the FOV 110 that is being assessed based on the output from the spectroscopy sensor 170 would need to be illuminated by the visible light source(s) 140. However, the distance D5 prevents an attempt to subvert operation of the spectroscopy sensor 170. Continuing the example, placement of living tissue such as a thumb directly over the spectroscopy sensor 170 would fail as that thumb would not be illuminated with a particular wavelength by the visible light source(s) 140. Trying to hold the thumb far enough from the spectroscopy sensor 170 to produce suitable output would then result in the thumb itself occluding part of the second FOV 110(2), occluding the IR camera 108(2) view. As a result, distance D5 improves the ability of the input device 104 to resist attempts to present false input.

In one implementation, the intensity data 172 is processed by the MWRS analysis module 174 to determine ratio data indicative of relative intensities of different pairs of wavelengths measured by the spectroscopy sensor 170. The ratio data is then assessed to determine the liveness data 176. In another implementation, the intensity data 172 may be processed by a trained machine learning system to determine the liveness data 176. In one implementation, the liveness data 176 is indicative of whether the object within the FOV 110(3) is deemed to be an actual user or an artifact. Operation of the MWRS analysis module 174 to determine the liveness data 176 is described in more detail with regard to FIG. 2. The liveness data 176 may be subsequently provided to other modules for use, such as the validity module 180, or other modules, as described below.

The input image data 112 may be processed by an image analysis module 152. The image analysis module 152 may comprise one or more previously trained machine learning modules or algorithmic modules that provide characteristic data 154 as output. The characteristic data 154 may include one or more of position data 156, pose data 158, sharpness data indicative of image sharpness, contrast data indicative of image contrast, or other data.

The position data 156 is indicative of a position of a portion of the user, such as the hand 102. In one implementation, the image analysis module 152 may comprise a first neural network that is trained to determine position data 156 indicative of a hand depicted in the input image data 112. For example, the position data 156 may indicate a position of the hand with respect to coordinates in the input image data 112. In other implementations other techniques may be used to determine position data 156. For example, an edge detector may be used to determine an edge of an object in the input image data 112, and a geometric center of the edges may be calculated.

The pose data 158 is indicative of a pose of the portion of the user, such as the hand 102. The pose may be indicative of one or more of orientation of the hand, articulation of one or more joints, and so forth. For example, the pose may specify one or more angles, relative to respective reference directions, of the hand. In another example, the pose may specify if the hand is closed (e.g. fist), open (fingers extended), and so forth. In one implementation, the image analysis module 152 may comprise a second neural network that is trained to determine pose data 158 of a hand depicted in the input image data 112. In other implementations other techniques may be used to determine pose data 158. For example, an edge detector may be used to determine an edge of an object in the input image data 112 and a total area bounded by the edge may be calculated. If the total area exceeds a threshold value, the input image data 112 may be deemed to have a first pose.

In other implementations, the image analysis module 152 may use other techniques or architectures to determine the characteristic data 154. For example, the image analysis module 152 may comprise a multi-headed neural network comprising a plurality of portions, having a first portion that determines the position data 156 and a second portion that determines the pose data 158 based on input image data 112.

A liveness trigger module 148 assesses one or more inputs and determines as output a liveness trigger 160. These inputs may include one or more of the distance data 146 or the characteristic data 154. The inputs are compared to respective threshold data 150.

The threshold data 150 may specify values or ranges of conditions that specify acceptance characteristics. The threshold data 150 may specify one or more of a minimum distance or a maximum distance of the distance data 146 for which operation of the one or more cameras 108 is to take place. The threshold data 150 may specify a threshold position of a hand 102 depicted in the input image data 112 which is deemed acceptable. For example, the threshold data 150 may specify an area specified by coordinates in the input image data 112, within which the position of the hand 102 is deemed acceptable. The threshold data 150 may specify a threshold pose of the hand 102 depicted in the input image data 112 that is deemed acceptable. For example, a pose indicative of an open hand, palm facing the camera 108 may be deemed acceptable. This process is discussed in more detail with regard to FIGS. 5A-5B.

When the liveness trigger module 148 determines that the inputs satisfy the conditions specified in the threshold data 150, a liveness trigger 160 is generated. The liveness trigger 160 may comprise a data message, interrupt signal, voltage change, and so forth. The liveness trigger 160 may be sent to a device control module 162.

In the implementation depicted here, the liveness trigger module 148 may generate the liveness trigger 160 based on one or more of the distance data 146, position data 156, or the pose data 158. For example, if an object has been detected at less than the maximum distance, has a hand position that is within the threshold position, and has a hand pose that is within the threshold pose, a liveness trigger 160 is generated and sent to the device control module 162.

The device control module 162 is configured to operate one or more of the devices of the input device 104. During operation, the device control module 162 may send control instructions 164 to one or more devices of the input device 104. For example, the device control module 162 may send control instructions 164 to operate one or more of the distance sensor 144, cameras 108, visible light sources 140, IR light sources 142, spectroscopy sensor 170, and so forth.

The device control module 162 may receive the liveness trigger 160, and responsive to the liveness trigger 160, send control instructions 164 to operate the MWRS hardware to determine the liveness data 176. For example, the device control module 162 may send control instructions 164 that operate one or more of the visible light sources 140 or the IR light sources 142 and the spectroscopy sensor 170 to determine the intensity data 172. The intensity data 172 may then be processed by the MWRS analysis module 174 to determine the liveness data 176.

A validity module 180 accepts one or more inputs and determines as output valid biometric input image data 182. Data acquired by the input device 104 may comprise timestamps indicative of when the data was acquired. In some implementations validity may be determined based on comparison of these timestamps. For example, input image data 112 that is acquired within a specified interval of a timestamp of the intensity data 172 that resulted in liveness data 176 indicative of an actual user may be deemed to be valid. In some implementations, the specified interval may begin before the acquisition of the intensity data 172 and end after the acquisition. In some implementations, the specified interval may be selected to provide assurance that it is too short to allow for substitution of an actual hand 102 in the FOV 110 with an artifact.

In addition to the liveness data 176, validity may also be based on continuity of presence of the hand 102. For example, even if within the specified interval, input image data 112 may be deemed invalid if acquired while the hand 102 is no longer within the threshold distance, the hand 102 has moved out of the threshold position, or is no longer in the threshold pose. Determination of the valid biometric input image data 182 is discussed in more detail with regard to the following figures.

The valid biometric input image data 182 may be subsequently processed. For example, the valid biometric input image data 182 may be processed to determine representation data. This is discussed in more detail with regard to FIG. 4.

Invalid biometric input image data may be disregarded. In some implementations, the invalid biometric input image data may be processed at least in part. For example, the invalid biometric input image data may be processed to determine information about an artifact for subsequent analysis.

In the implementation depicted, the hand 102 is held above the input device 104, with the FOV 110(1)-(3) extending upward. In other implementations, other configurations may be used. For example, the FOV 110(1)-(3) may extend downwards, and the user may place their hand 102 in the FOV 110 under the input device 104.

In the implementation depicted here, the input device 104 does not include a guide, scan plate, or other structure that constrains the pose or position of the hand 102. The omission of the guide may improve sanitary operation of the system. For example, by removing the guide, the user's hand 102 does not come into physical contact with a structure, eliminating the possibility of contact transmission of contaminants, disease, and so forth. By removing the physical contact, the need for surface cleaning of the guide between users may be eliminated.

In another implementation, the input device 104 may include a structure such as a guide or scan plate to constrain at least some movement of the hand 102. For example, the scan plate may comprise a flat pane of glass which the hand 102 may rest upon, and the camera 108 may then acquire an image.

In the implementation depicted here, the input device 104 does not include a hood, cover, or other structure that blocks at least a portion of the ambient light from reaching one or more of the camera 108 or the spectroscopy sensor 170. The omission of the hood may improve usability and accessibility of the system by users. For example, by omitting the hood, the user's hand 102 may be moved in any direction with respect to the input device 104 to bring the hand 102 into the FOV 110(1)-(3). In contrast, a hood and associated support structure would limit the directions, relative to the input device 104, from which the user may present their hand 102.

One or more of the modules described above may be executed on other computing devices 106(N). In one implementation, the validity module 180 may be executed on a computing device 106(2), such as a server. One or more of the characteristic data 154, liveness data 176, input image data 112, information based on the input image data 112, or other information may be provided to a computing device 106(2).

The systems and techniques described above are discussed with respect to images of human hands. These systems and techniques may be used with respect to other forms of data, other kinds of objects, and so forth. For example, these techniques may be used for facial recognition systems, object recognition systems, and so forth.

Figure 2:
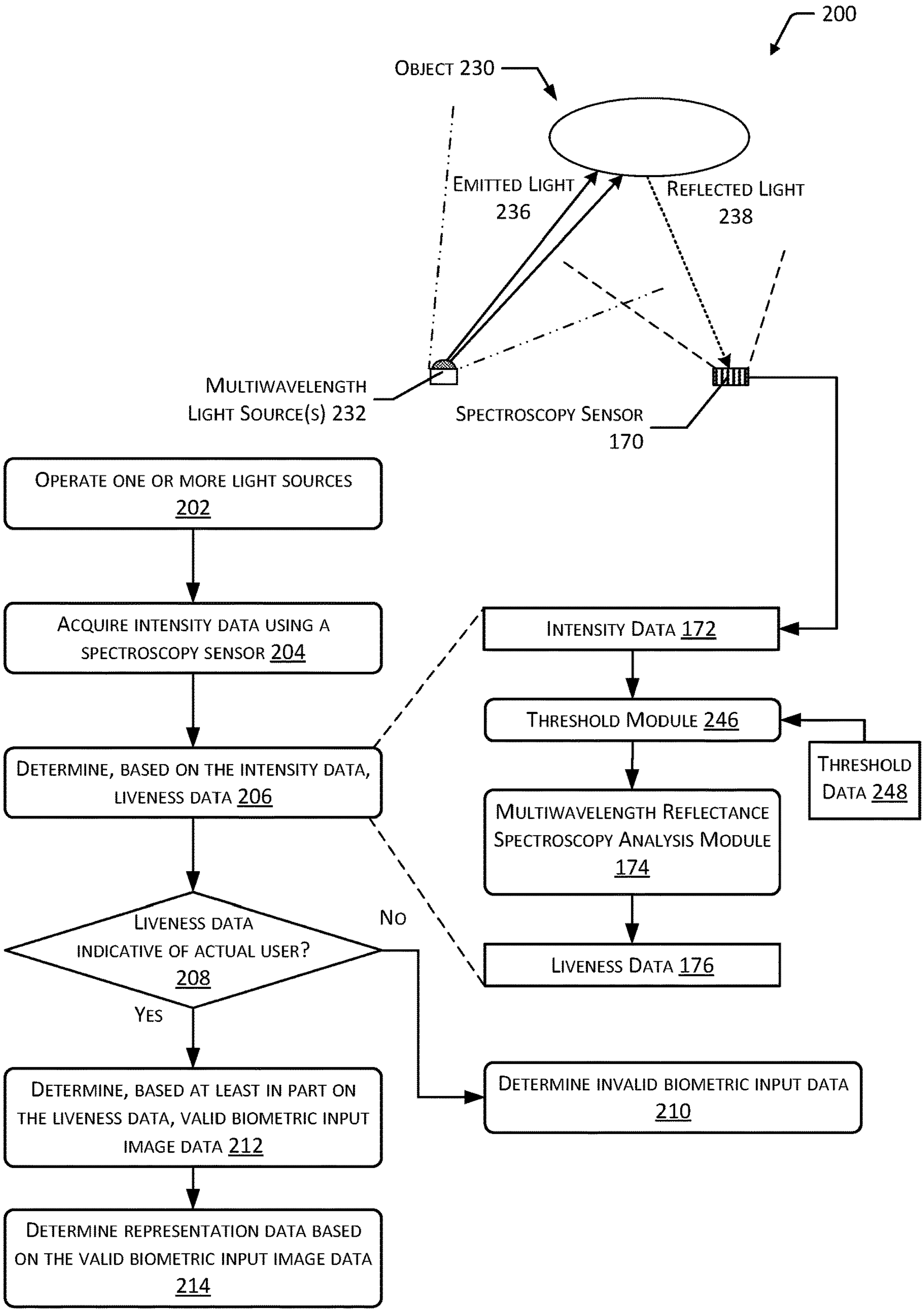
FIG. 2 is a flow diagram of a process to determine liveness data using multiwavelength reflectance spectroscopy and valid biometric input image data, according to some implementations.

FIG. 2 is a flow diagram 200 of a process to determine liveness data 176 using multiwavelength reflectance spectroscopy and valid biometric input image data 182, according to some implementations. In some implementations the process may be implemented by the input device 104.

At 202 one or more multiwavelength light sources 232 are operated to illuminate the FOV 110 with emitted light 236 comprising a first plurality of wavelengths of light. The multiwavelength light sources 232 may comprise one or more of the visible light sources 140 or the IR light sources 142. The emitted light 236 interacts with and may be reflected by an object 230 as reflected light 238.

In one implementation brightness of the one or more light sources remains fixed during a timeslot. For example, the one or more light sources may be operated with a brightness level that produces maximum light output.

In some implementations, brightness of the emitted light 236 from the one or more light sources may be based on distance data 146 provided by the distance sensor 144 that is indicative of distance D1 between an object 230 and the distance sensor 144. For example, brightness level may be determined based on the distance data 146. The one or more light sources are then operated according to the brightness level. As the distance D1 increases, the brightness level and corresponding brightness of the one or more light sources may be increased. An increase in brightness results in increased emission of photons per unit of time. By controlling the brightness of the one or more light sources (or other light sources), a particular optical power per unit area of the object 230 may be obtained. By obtaining a particular optical power per unit area of the object 230, and dynamically adjusting the brightness to account for variations in distance D1, the overall quality of intensity data 172 may be improved, improving the accuracy of the resulting determination as to whether the user is present.

In some implementations, the output intensity of one or more of the light sources may be confirmed or determined based on a measurement of electrical current used by the one or more light sources during operation. An anomalous condition may be deemed to have occurred if the intensity of incident light as measured by the spectroscopy sensor 170 exceeds an expected intensity based on the electrical current drawn by the one or more multiwavelength light sources 232 and their respective operating wavelengths.

At 204 intensity data 172 indicative of the reflected light 238 is acquired by the spectroscopy sensor 170.

In one implementation the spectroscopy sensor 170 may comprise a photodetector used to acquire intensity data 172 and may utilize the multiwavelength light sources 232 to provide a timed sequence of illumination at specific wavelengths. For example, at a first time the visible light sources 140 may be operated to illuminate the third FOV 110(3) with light having a wavelength of 415 nanometers (nm) and first intensity data 172(1) is acquired using the photodetector. Continuing the example, at a second time the visible light sources 140 are operated to illuminate the third FOV 110(3) with light having a wavelength of 445 nm and second intensity data 172(2) is acquired using the photodetector.

In another implementation the spectroscopy sensor 170 may comprise a multispectral sensor comprising a plurality of photodetectors, each with a respective filter that passes light with a particular wavelength. For example, a first detector portion may comprise a first filter and a first photodetector, a second detector portion may comprise a second filter and a second photodetector, and so forth. The multispectral sensor may be used to acquire intensity data 172 with respect to a plurality of wavelengths during a single sample interval. For example, at a first time the visible light sources 140 may be operated to illuminate the third FOV 110(3) with light having a wavelength of 415 nm and light having a wavelength of 445 nm. The multispectral sensor may be used to acquire first intensity data 172(1) associated with 415 nm and second intensity data 172(2) associated with 445 nm.

In some implementations, a calibration process (not shown) may be performed before use. For example, calibration may be performed using an object comprising a color calibrated material, or a material with a known reflectance such as SPECTRALON by Labsphere, Inc.

The input device 104 is able to determine the intensity data 172 under a variety of different ambient lighting conditions. Ambient lighting may vary in wavelength composition, color temperature, illumination level, and so forth. For example, the system may be used to acquire the intensity data 172 in ambient lightning ranging from dim to several times that of solar illumination. As a result, the input device 104 may be used outdoors, indoors within areas that are exposed to sunlight such as near windows, in the presence of high intensity artificial illumination, and so forth.

Depending upon the composition of the object 230, different intensities of reflected light 238 will be produced. For example, molecules in human tissue such as hemoglobin, melanin, lipids, and so forth reflect light of different colors differently than other molecules such as silicone, dyes, and so forth.

At 206, based on the intensity data 172, the liveness data 176 is determined. The liveness data 176 is indicative of an assessment of the object 230. For example, the liveness data 176 may indicate that a user is deemed to be an actual hand 102 and present, or that an artifact has been presented and no user is deemed to be present. The liveness data 176 may be considered an indication of "liveness", indicating whether an actual person is present at the input device 104 at the time the intensity data 172 was acquired.

In some implementations, a threshold module 246 may assess the intensity data 172 before further processing. The threshold module 246 may comprise the intensity data 172 or information therein with one or more thresholds specified by threshold data 248. In one implementation, a minimum count of samples of intensity data 172 may be specified by the threshold data 248. If the count of samples in the intensity data 172 is less than the threshold minimum count of samples of intensity data 172, the process may stop. In contrast, if the count of samples in the intensity data 172 is greater than or equal to the threshold minimum count of samples of intensity data 172, the process may proceed to the MWRS analysis module 174.

In another implementation, a minimum intensity value may be specified by the threshold data 248. If the intensity value of a sample of the intensity data 172 is less than the threshold minimum intensity value, the sample may not be processed further. In contrast, if the intensity value of the sample of the intensity data 172 is greater than or equal to the threshold minimum intensity value, the process may proceed to the MWRS analysis module 174. A maximum intensity value may also be specified and used in a similar fashion.

In one implementation, the intensity data 172 may comprise intensity values for sample wavelengths that have been adjusted to account for background intensity values. In other implementations, unadjusted or "raw" intensity values for the sample wavelengths may be used. The comparisons with respect to one or more of the count or intensity may be used with respect to one or more of the adjusted values or the unadjusted values.

In one implementation the liveness data 176 may be determined by assessing intensity ratios of various wavelengths of light. The intensity data 172 is indicative of the intensity values associated with different wavelengths. For example, the intensity data 172 may indicate infrared (940 nm) "89", green (515 nm) "7", blue (455 nm) "32", and violet (415 nm) "13".

A ratio module may use the intensity data 172 passed by the threshold module 246 to determine ratio data indicative of one or more ratio values. The ratio values may be determined by dividing a first intensity value of a first wavelength by a second intensity value of a second wavelength. In some implementations, the second wavelength may comprise a reference wavelength that is used for all ratios. For example, the reference wavelength may be one of violet (415 nm), infrared (940 nm), or other wavelength of the sample wavelengths.

In some implementations, a correction factor may be determined based on the distance data 146 indicative of the distance D1 between the input device 104 and the object 230. The correction factor may be calculated, retrieved from a lookup table, and so forth. The correction factor may be used to adjust one or more of the intensity data 172 or ratio data. For example, a first uncorrected intensity value may be multiplied by a first correction factor to determine the first intensity value. In another example, a first uncorrected ratio value may be multiplied by a second correction factor to determine a first ratio value. Different correction factors may be associated with intensity data 172 for a particular wavelength, particular ratios, and so forth.

In one implementation, the MWRS analysis module 174 may process the ratio data to determine the liveness data 176. In one implementation, each ratio value within the ratio data may be compared to respective threshold values, and the output used to determine the liveness data 176 as illustrated in the following table:

TABLE 1

| Ratio data | Ratio Value | Comparison | Threshold Value | Output |
|---|---|---|---|---|
| Infrared/Violet | value1 | > | value2 | True |
| Green/Infrared | value3 | < | value4 | True |
| Blue/Violet | value5 | > | value6 | True |
| Liveness data 176 | — | — | — | User Present |

In the implementation shown with regard to TABLE 1, the outputs from the respective comparisons are combined using an AND function. If each output is true, then the liveness data 176 is indicative of user presence. If any of the outputs is false, the liveness data 176 would be indicative of no user present. In other implementations, the determination of the liveness data 176 may utilize other functions. For example, a weighted average of the outputs may be calculated and used to determine the liveness data 176.

In some implementations, the distance data 146 indicative of distance D1 may be used to determine one or more of the threshold values for one or more of the comparisons. For example, a threshold correction factor may be retrieved from a lookup table or calculated based on the distance D1 as indicated by the distance data 146. The threshold value used for a comparison may comprise the product of an initial threshold value and the threshold correction factor. As the distance changes, the threshold value used for the comparison may also change.

In other implementations, other techniques may be used. For example, the MWRS analysis module 174 may utilize a classifier that uses the ratio data as input to provide the liveness data 176 as output. In another example, a trained machine learning system may accept as input one or more of the intensity data 172 or the ratio data, and provide as output the liveness data 176. In other implementations, other techniques may be used instead of or in addition to analysis of ratios. For example, relative intensity values or absolute intensity values may be assessed to determine the liveness data 176.

In some implementations the threshold values may be adjusted. This adjustment may be performed to adjust for users with different compositions. For example, the input device 104 may acquire and used invalid biometric input image data to determine an unvalidated user identity. Based on the unvalidated user identity, one or more threshold values may be determined. The intensity data 172 may then be re-assessed using the MWRS analysis module 174 to determine the liveness data 176.

Other techniques may be used by the MWRS analysis module 174 to determine the liveness data 176. For example, the intensity data 172 or the ratio data may be considered coordinates indicative of a point within an n-dimensional space. Within the n-dimensional space, a first volume may be associated with user presence. The liveness data 176 may be determined based on whether the intensity data 172 or the ratio data is indicative of a point that is within the first volume. A confidence value may be determined that is indicative of a likelihood that the liveness data 176 is correct. In one implementation, the confidence value may be based on a distance between the coordinates of the intensity data 172 or the ratio data and a specified point within the n-dimensional space. For example, the closer the point described by the intensity data 172 or the ratio data is in the n-dimensional space to a center of the first volume, the greater the confidence value.

At 208 a determination is made as to whether the liveness data 176 is indicative of an actual user. If no, the processes may proceed to 210. At 210 invalid biometric input image data is determined. In some implementations, mitigating actions may be then be performed. If yes, the process may proceed to 212.

At 212 valid biometric input image data 182 is determined based at least in part on the liveness data 176. This determination is discussed in more detail beginning with FIG. 3.

At 214 representation data is determined based on the valid biometric input image data 182. This determination is discussed in more detail with regard to FIG. 4.

Figure 3:
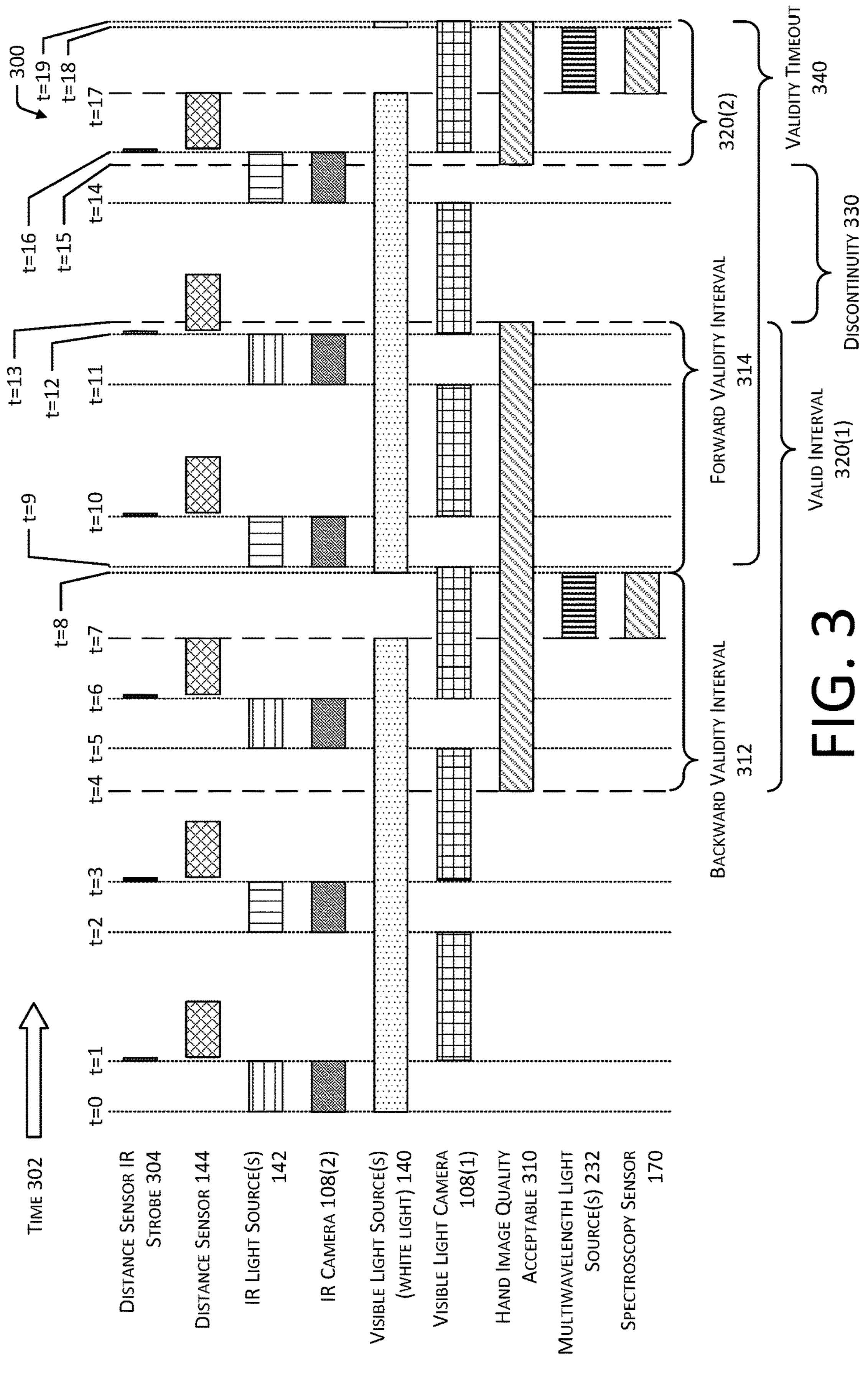
FIG. 3 illustrates a timeline of operation of various components of the input device, according to some implementations.

FIG. 3 illustrates at 300 a timeline of operation of various components of the input device 104, according to some implementations. In this illustration time 302 increases from left to right. To improve legibility and not as a limitation, the duration of individual events as indicated by their width in this figure are not to scale. The device control module 162 may operate the various devices according to the timing described herein.

Depicted are operation of a distance sensor IR strobe 304 and detector of a distance sensor 144. As described above, the distance sensor 144 may comprise an optical time-of-flight sensor that emits an IR strobe and uses a detected reflection to determine a distance to an object.

Depicted are IR light sources 142 and the IR camera 108(2). The IR light sources 142 illuminate the FOV 110(2) of the IR camera 108(2). As described above, the IR light sources 142 may include polarizers and provide different polarizations of emitted light. In this illustration, different polarizations are depicted by different crosshatch patterns.

Depicted are visible light sources 140 and the visible light camera 108(1). The visible light sources 140 may be operated to illuminate the FOV 110(1) of the visible light camera 108(1) with white light.

Depicted at 310 are times during which hand image quality is determined to be acceptable. For example, hand image quality may be deemed acceptable when the hand is within a specified position and within a specified pose. During operation, input image data 112 may be processed by the image analysis module 152 to determine the characteristic data 154. For example, while input image data 112 is being acquired, the image analysis module 152 may process that acquired input image data 112. This determination is discussed in more detail with regard to FIGS. 5A-5B. The determination that hand image quality is acceptable 310 may result in operation of the MWRS hardware to determine the liveness data 176. For example, the multiwavelength light source(s) 232 and the spectroscopy sensor 170 may be operated to acquire intensity data 172.

Depicted are the multiwavelength light source(s) 232 operated during acquisition of the intensity data 172. The multiwavelength light source(s) 232 may comprise one or more of the visible light sources 140, or the IR light sources 142. The multiwavelength light source(s) 232 may be operated to emit light in one or more of a time sequence of illumination at specific wavelengths, or a plurality of wavelengths emitted at the same time. In one implementation, the multiwavelength light source(s) 232 may comprise one or more visible light sources 140 that are operated to emit particular wavelengths, such as green (516 nm), blue (455 nm), and violet (416 nm). In this implementation, green may be emitted for a first time interval, blue for a second time interval, and violet for a third time interval, with respective intensity data 172 for each color obtained during the respective time intervals.

Depicted is the spectroscopy sensor 170 operated during acquisition of the intensity data 172. To acquire the intensity data 172, the multiwavelength light source(s) 232 and the spectroscopy sensor 170 are operated at the same time.

In the implementation depicted, the distance sensor IR strobe 304 and distance sensor 144 are operated at scheduled intervals. The distance IR strobe 304 is operated beginning at times t=1, 3, 6, 10, 12, and 16, and the distance sensor 144 operates immediately thereafter.

In the implementation depicted, the IR light sources 142 and IR camera 118(2) are operated at scheduled intervals. The IR light sources 152 and IR camera 108(2) are operated at time intervals t=0-1, 2-3, 5-6, 9-10, 11-12, and 14-16. As mentioned above, different polarizations may be used to acquire IR image data 116 with different modalities. For example, a first polarization of IR light source 142 may be operated at time intervals t=0-1, 5-6, and 11-12. Continuing the example, a second polarization of IR light source 142 may be operated at time intervals t=2-3, 9-10, and 14-16.

In the implementation depicted, the visible light sources 140 are operated to emit white light during operation, except during acquisition of the intensity data 172. For example, the visible light sources 140 are operated to emit white light from time interval t=0-7, then time interval t=8-17, and then t=18-19.

In the implementation depicted, the visible light camera 108(1) is operated at scheduled time intervals t=1-2, 3-5, 6-9, 10-11, 12-14, 16-19.

In the implementation depicted, the MWRS hardware comprising the multiwavelength light sources 232 and the spectroscopy sensor 170 are operated during the time intervals of t=7-8 and t=17-18. Operation of the MWRS hardware in this implementation is performed during operation of the visible light camera 108(1) and avoids time intervals during which either the distance sensor 144 or the IR camera 108(2) is operated. In other implementations this may be reversed.

Upon determining that hand image quality is acceptable 310, the input device 104 may operate the MWRS hardware at the next available interval to determine liveness data 176. For example, at t=4 hand image quality is deemed to be acceptable. The next available time interval after t=4, given the above mentioned limitations, to operate the MWRS hardware would begin at t=7.

Overlapping operation of the MWRS hardware may affect operation of other components that are sensitive to the different illumination provided by the multiwavelength light sources 232. For example, a time sequence of different wavelengths of visible light emitted during operation of the visible light camera 108(1) may adversely affect the visible light image data 114 acquired by the visible light camera 108(1) at the same time.

In this illustration, the hand image quality deemed acceptable 310 begins at t=4. Responsive to this, the MWRS hardware is scheduled to operate at t=7 to determine intensity data 172. The intensity data 172 is determined, and processed by the MWRS analysis module 174 to determine liveness data 176. Meanwhile, input image data 112 continues to be acquired. The input image data 112, and other sensor data such as the intensity data 172, are associated with respective timestamps or other indicia indicative of when they were acquired.

In the example depicted, the liveness data 176 determined based on the intensity data 172 indicates an actual user's hand 102 is present, and not an artifact. A validity interval may be specified with respect to the time associated with the liveness data 176, or the intensity data 172 that the liveness data 176 is based on. The timestamp may be associated with a beginning, end, or other part of a specified interval. In this illustration the liveness data 176 may be associated with the time t=8, the conclusion of the interval used to acquire the intensity data 172.

In this illustration, a forward validity interval 314 extends from the timestamp associated with the liveness data 176 indicative of an actual user to a later time. For example, the forward validity interval 314 extends from t=8 until t=13. The forward validity interval 314 may continue until a timeout or maximum interval value is reached, or until the hand image quality is deemed to be unacceptable. In this illustration, the hand image quality is no longer acceptable at t=13, resulting in the end of the forward validity interval 314.

Also depicted in this illustration, is a backward validity interval 312 that extends from the timestamp associated with the liveness data 176 indicative of an actual user to an earlier time. For example, the backward validity interval 312 extends from t=4 until t=8. The backward validity interval 312 may retroactively begin at a maximum interval value before the starting time, or at a time when the hand image quality is deemed to be acceptable 310. In this illustration, the hand image quality before t=8 is deemed acceptable 310 at t=4 and serves as the beginning of the backward validity interval 312 that concludes at the validity timestamp of t=8.

A valid interval 320 is also depicted. The valid interval 320 may comprise one or more of the forward validity interval 314 or the backward validity interval 312. For example, a valid interval 320(1) may extend from t=4 to t=13. Another valid interval 320(2) extends from t=15-19.

Input image data 112 acquired during a valid interval 320 may be deemed to be valid biometric input image data 182 and used for subsequent processing.

In some situations, a discontinuity 330 in the input image data 112 may occur. A discontinuity 330 may result from the hand image quality no longer being deemed to be acceptable, or other conditions. For example, if the distance data 146 indicates that the distance D1 is less than a minimum distance or greater than a maximum distance, a discontinuity 330 may be determined. In another example, if the user closes their hand, producing a fist, the resulting input image data 112 would not depict a threshold pose and result in the hand image quality being deemed unacceptable. Because a discontinuity 330 may be associated with an attempt to subvert operation of the input device 104 and introduce an artifact, input image data 112 acquired at a time associated with a discontinuity 330 may be deemed invalid.

Once a discontinuity 330 has been determined, after an initial startup, after a reset, and so forth, subsequent determinations of validity may be performed. For example, as depicted here at time t=15 the hand image quality is deemed to be acceptable 310 and the MWRS hardware is scheduled to acquire second intensity data 172 at t=17-18. Continuing the example, second liveness data 176 based on the second intensity data 172 is indicative of an actual user, and so a validity interval 320(2) comprising a second backward validity interval 312(2) is determined.

Figure 4:
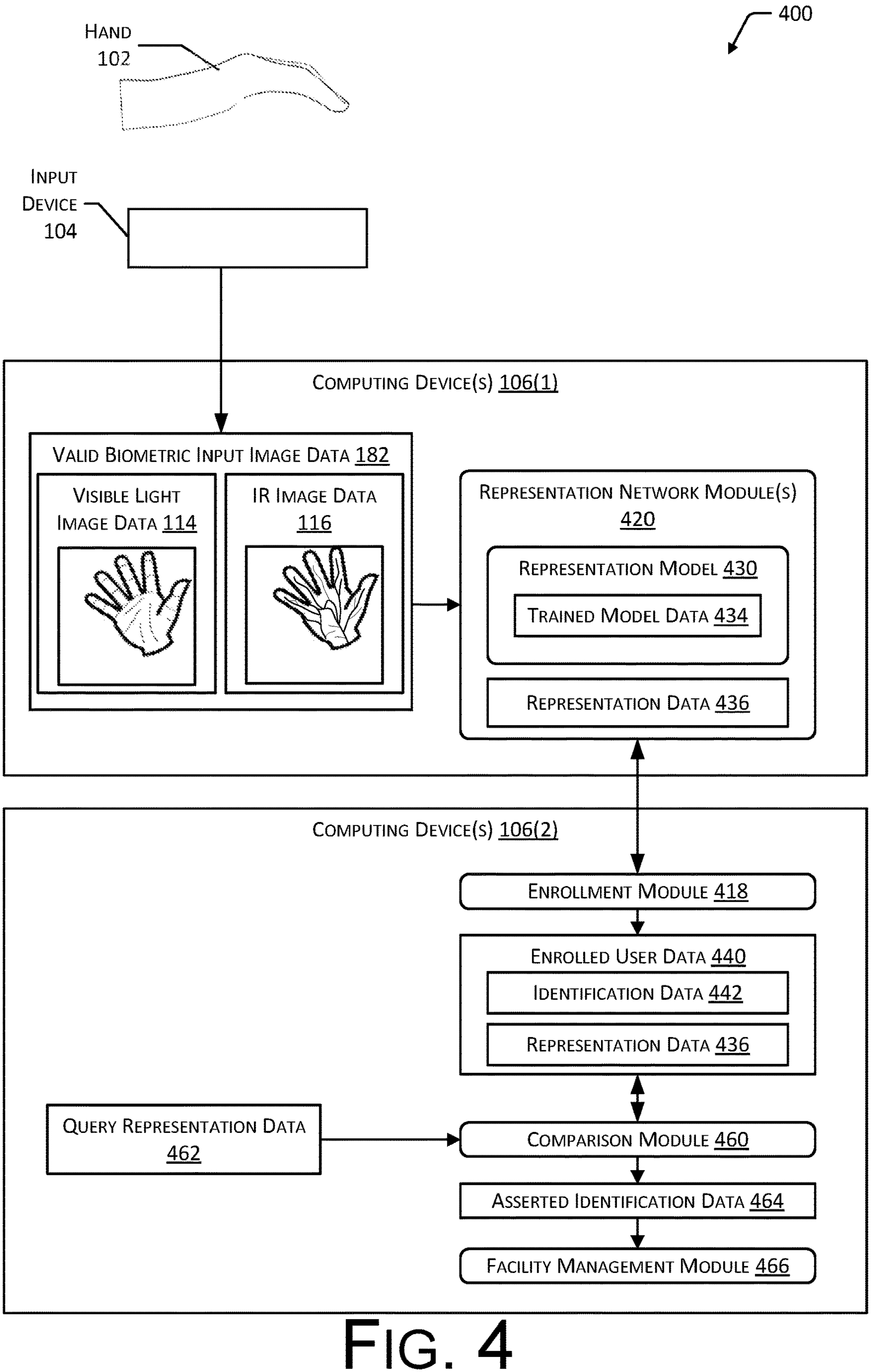
FIG. 4 illustrates a system including the input device and another computing device to determine asserted identification data, according to some implementations.

FIG. 4 illustrates a system 400 including the input device 104 and another computing device to determine asserted identification data, according to some implementations. Users may be able to utilize the system 400 by performing an enrollment process. An enrollment module 418 may coordinate the enrollment process. Enrollment may associate biometric information, such as representation data or transformed representation data, with particular information such as a name, account number, and so forth.

During an enrollment process, the user opts in and presents their hand 102 to the input device 104. The input device 104 determines the liveness data 176. In some implementations, based on the liveness data 176 various actions may be taken. For example, if the liveness data 176 indicates an actual hand is present, the input device 104 may then provide valid biometric input image data 182 to a computing device 106(1) executing a representation network module 420. Continuing the example, the computing device 106(1) of the input device 104 may generate an error and present an error notification using an output device. In another example, the liveness data 176 and the valid biometric input image data 182 may be provided to the computing device 106(1) regardless of the value of the liveness data 176.

The representation network module 420 may comprise a neural network implementing one or more representation models 430 ("representation model") that accepts as input the valid biometric input image data 182 and provides as output representation data 436. The representation model 430 comprises a machine learning network ("network") that is trained to determine representation data 436 based on valid biometric input image data 182. The network may comprise a convolutional neural network, deep learning network, or other network architecture. The representation data 436 is representative of at least some of the features depicted in the valid biometric input image data 182. In some implementations, the representation data 436 may comprise a vector value in an embedding space.

In some implementations the representation network module 420 may also accept as input other data. For example, one or more of the characteristic data 154 or the liveness data 176 may be provided to the representation network module 420. The representation network module 420 may use this or other data to further assess the valid biometric input image data 182, determine a confidence value associated with the representation data 436, and so forth.

In some implementations, the computing device 106(1) of the input device 104 may include and may execute the (trained) representation network module(s) 420. In another implementation, the input device 104 may encrypt and send the valid biometric input image data 182 or data based thereon, the liveness data 176, or other data to another computing device 106(2) such as a server.

During the enrollment process, the submitted representation data 436 may be checked to determine whether the user has been previously enrolled. A successful enrollment may comprise storage of identification data 442, such as name, telephone number, account number, and so forth and storage of one or more of the representation data 436 or the transformed representation data as enrolled user data 440. In some implementations, the enrolled user data 440 may comprise additional information associated with processing of the valid biometric input image data 182 with a representation model 430. For example, the enrolled user data 440 may comprise intermediate layer data, such as the values of a penultimate layer of the representation model 430.

In this illustration, at a first time the representation model 430 is trained using training data to determine trained model data. The training data may comprise a plurality of first modality and second modality images that have been labeled. For example, label data may indicate the sample identifier, identity label, modality label, and so forth.

During subsequent usage, such as at a second time, the (as yet unidentified) user presents their hand 102 at an input device 104. As described above with regard to enrollment, the input device 104 determines the liveness data 176. In some implementations, based on the liveness data 176 various actions may be taken. For example, if the liveness data 176 indicates an actual hand is present, the input device 104 may then provide valid biometric input image data 182 to the computing device 106(2) for further processing. Continuing the example, the computing device 106(1) of the input device 104 may generate an error and present an error notification using an output device. In another example, the liveness data 176 and the valid biometric input image data 182 may be provided to the computing device 106(2) regardless of the value of the liveness data 176.

The resulting query valid biometric input image data 182 may be processed by the (now trained) representation model 430 to determine query representation data 462.

The comparison module 460 compares the query representation data 462 to the representation data 436 stored in the enrolled user data 440 to determine asserted identification data 464. In one implementation, the asserted identification data 464 may comprise a user identifier associated with the closest previously stored representation data 436 in the enrolled user data 440 to the query representation data 462 associated with the user who presented their hand 102. The comparison module 460 may utilize other considerations, such as requiring that the query representation data 462 is no more than a maximum distance in the representation space from the representation data 436 of a particular user before determining the asserted identification data 464. In some implementations the asserted identification data 464 may include the liveness data 176 or information based thereon. For example, if the liveness data 176 indicates that the valid biometric input image data 182 is associated with an artifact, the asserted identification data 464 may be indicative of this.

The asserted identification data 464 may then be used by subsequent systems or modules. For example, if the liveness data 176 indicates the valid biometric input image data 182 is associated with a real hand, the asserted identification data 464, or information based thereon, may be provided to a facility management module 466. In another example, if the liveness data 176 indicates the valid biometric input image data 182 is associated with an artifact, the system 400 may provide a request for additional information at the input device 104, create an entry in an error log, flag the asserted identification 464 as potentially compromised, and so forth.

The facility management module 466 may use the asserted identification data 464 to associate an identity with that user as they move about the facility. For example, the facility management module 466 may use data from cameras or other sensors in the environment to determine a location of the user. Given a known path of the user from an entrance that utilizes the input device 104, the user identity indicated in the identification data 442 may be associated with the user as they use the facility. For example, the now identified user may walk to a shelf, remove an item, and leave the facility. The facility management module 466 may determine the interaction data indicative of the removal of the item as being associated with the user identifier specified in the asserted identification data 464, and bill an account associated with the user identifier. In another implementation, the facility management module 466 may comprise a point of sale system. The user may present their hand 102 at checkout to assert their identity and pay using a payment account that is associated with their identity.

Figure 5A:
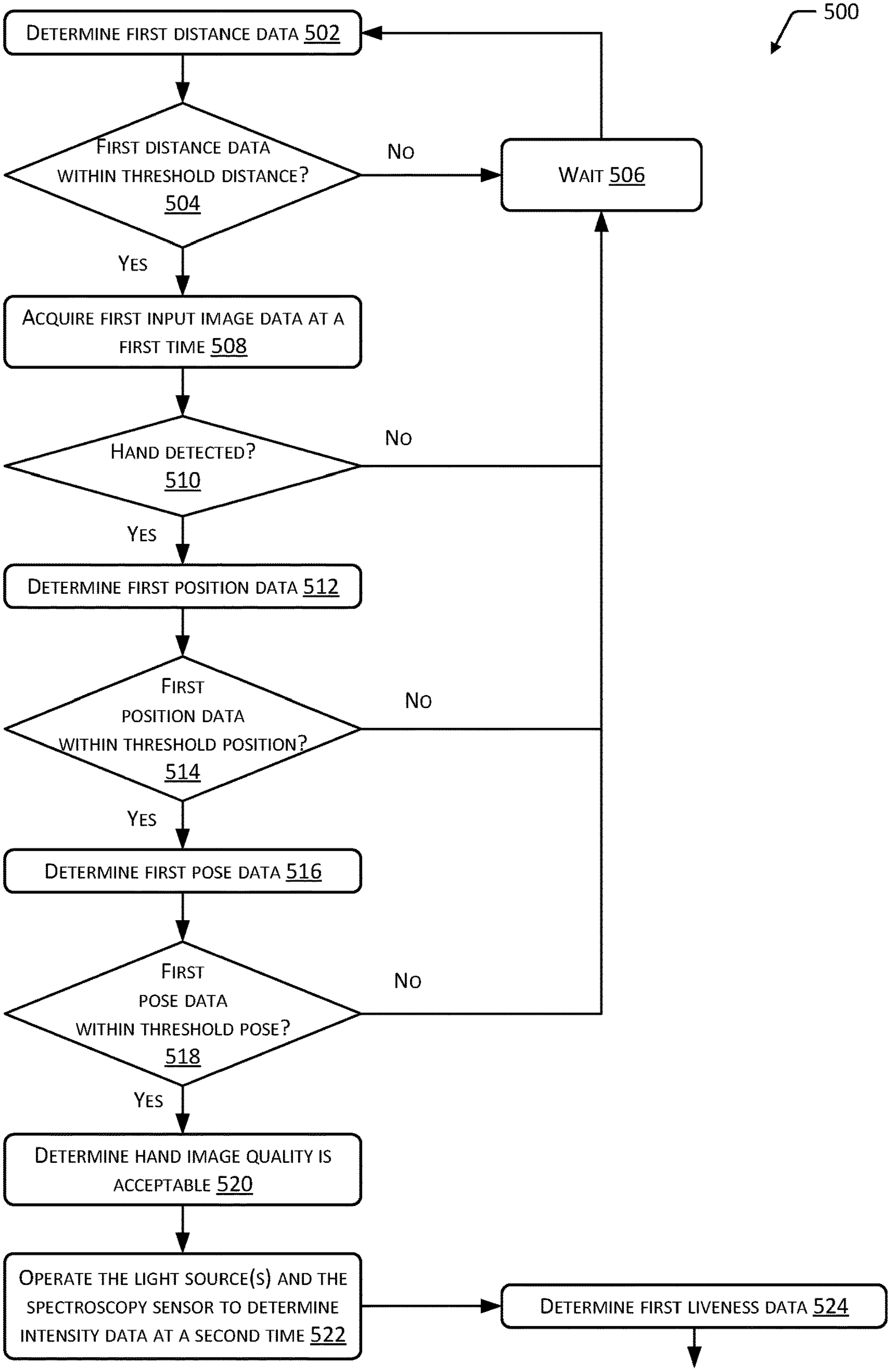
FIGS. 5A-5B depict a flow diagram of a process to trigger liveness detection and determination of representation data at the input device, according to some implementations.
Figure 5B:

FIGS. 5A-5B depict a flow diagram of a process 500 to trigger liveness detection and determination of representation data 436 at the input device 104, according to some implementations.

At 502 first distance data 146 is determined. For example, the distance sensor 144 may be operated with the distance sensor IR strobe 304 to determine first distance data 146.

At 504 a determination is made as to whether the first distance data 146 is within a threshold distance. For example, the first distance data 146 may be compared to a threshold range comprising a minimum distance value and a maximum distance value. If not, the process may proceed to 506. At 506 the system may wait for a specified time and then proceed to 502. If yes, the process may proceed to 508.

At 508 first input image data 112(1) is acquired at a first time. For example, one or more of the visible light camera 108(1) or the IR camera 108(2) and the associated light sources may be operated.

For ease of illustration, and not as a limitation, in some implementations one or more image filtering processes (not shown) may be used to disregard images from further processing. For example, characteristic data 154 such as sharpness, contrast, and so forth may be assessed. Input image data 112 that does not meet specified threshold values, such as a minimum sharpness value, contrast within a threshold range, and so forth may be disregarded from further processing.

At 510 the first input image data 112(1) is processed to determine if a hand is detected. The first input image data 112(1) may be processed by a previously trained machine learning system, such as a trained neural network, classifier, and so forth to determine data indicative of whether a hand is depicted in the image. In some implementations 510 may be omitted and the process may proceed to 512. If a hand is not detected, the process may proceed to 506. If a hand is detected, the process proceeds to 512.

At 512 first position data 156 is determined. The first position data 156 is indicative of a position of a portion of the user, such as the hand 102, as depicted in the input image data 112. In one implementation, the image analysis module 152 may comprise a first neural network that is trained to determine first position data 156 indicative of a hand depicted in the input image data 112. For example, the first position data 156 may indicate a position of the hand with respect to coordinates in the first input image data 112(1). In other implementations other techniques may be used to determine first position data 156. For example, an edge detector may be used to determine an edge of an object in the input image data 112, and a geometric center of the edges may be calculated.

At 514 a determination is made as to whether the first position data 156 is within a threshold position. For example, the first position data 156 may specify a center of the palm of the hand 102 and the threshold position may specify a set of coordinates that define a rectangle. If the first position data 156 indicates a location that is within the rectangle, it may be deemed to be within the threshold position. If the first position data 156 is deemed to not be within the threshold position, the process may proceed to 506. If the position data 156 is deemed to be within the threshold position, the process may proceed to 516.

The threshold position associated with the operation of the MWRS hardware may differ from that associated with further processing, such as to determine the representation data 436. As described with regard to FIG. 1, the third FOV 110(3) of the spectroscopy sensor 170 may differ from one or more of the first FOV 110(1) of the visible light camera 108(1) or the second FOV 110(2) of the IR camera 108(2). As a result, the threshold position for operation of the MWRS hardware may differ from that used to acquire input image data 112 that is subsequently processed by the representation network module(s) 420.

At 516 first pose data 158 is determined. The first pose data 158 is indicative of a pose of the portion of the user, such as the hand 102, as depicted in the first input image data 112(1). The pose may be indicative of one or more of orientation of the hand, articulation of one or more joints, and so forth. For example, the pose may specify one or more angles, relative to respective reference directions, of the hand. In another example, the pose may specify if the hand is closed (e.g. fist), open (fingers extended), and so forth. In one implementation, the image analysis module 152 may comprise a second neural network that is trained to determine pose data 158 of a hand depicted in the input image data 112. In other implementations other techniques may be used to determine pose data 158. For example, an edge detector may be used to determine an edge of an object in the input image data 112 and a total area bounded by the edge may be calculated. If the total area exceeds a threshold value, the input image data 112 may be deemed to have a first pose.

At 518 a determination is made as to whether the first pose data 158 is within a threshold pose. For example, the first pose data 158 may indicate an articulation of the hand 102, such as palm open, rotation of the hand 102 with respect to one or more axes, and so forth. The threshold pose may specify a particular articulation, such as palm open, rotation that is less than a threshold number of degrees with respect to a first axis, and so forth. If the pose data 158 indicates a pose that has the specified articulation and is within a specified rotation range, it may be deemed to be within the threshold pose. If the first pose data 158 is deemed to not be within the threshold pose, the process may proceed to 506. If the first pose data 158 is deemed to be within the threshold pose, the process may proceed to 520.

At 520 the hand image quality is deemed to be acceptable 310. The hand image quality may be deemed to be acceptable 310 as of a specified timestamp, such as the timestamp associated with the acquisition of the input image data 112. As described above, responsive to the characteristic data 154, the liveness trigger module 148 may generate a liveness trigger 160.

At 522 the multiwavelength light source(s) 232 and the spectroscopy sensor 170 are operated at a second time to determine intensity data 172, as described previously. For example, responsive to the liveness trigger 160, the device control module 162 may determine control instructions 164 to operate the multiwavelength light source(s) 232 and the spectroscopy sensor 170.

At 524 first liveness data 176 is determined. For example, based on the first intensity data 172 the MWRS analysis module 174 determines the first liveness data 176. As described with regard to FIG. 3, if the first liveness data 176 is indicative of an actual user, a valid interval 320 may be determined. The valid interval 320 may comprise one or more of the backward validity interval 312 or the forward validity interval 314. For example, with regard to the backward validity interval 312, the first input image data 112(1) acquired during that time interval may be deemed to be valid biometric input image data 182.

In some implementations the process may proceed to FIG. 5B. The process of FIG. 5B may be used to determine a discontinuity, and to determine the forward validity interval 314.

The input device 104 may continue to acquire input image data 112 during operation. The subsequent input image data 112 may be assessed based on the liveness data 176 and a determination of discontinuities 330 to determine the valid biometric input image data 182.

At 552 second distance data 146 is determined, after the second time.

At 554 second input image data 112(2) is acquired at a third time.

As described above, in some implementations one or more image filtering processes (not shown) may be used to disregard images from further processing. For example, characteristic data 154 such as sharpness, contrast, and so forth may be assessed. Input image data 112 that does not meet specified threshold values, such as a minimum sharpness value, contrast within a threshold range, and so forth may be disregarded from further processing.

At 556 a determination is made as to whether the second distance data 146 is within a threshold distance. If no, a discontinuity 330 may be deemed to have occurred, and the process may proceed to 558. If yes, the process may proceed to 580.

At 558 the second input image data 112(2) may be deemed to be invalid. Responsive to this determination of invalidity, the process may proceed to 560. Also responsive to this determination of invalidity, other operations may be performed. For example, the second input image data 112(2) may be disregarded, deleted, and so forth.

At 560 the multiwavelength light source(s) 232 and the spectroscopy sensor 170 are operated at a fourth time to determine second intensity data 172.

At 562 second liveness data 176 is determined. For example, based on the second intensity data 172 the MWRS analysis module 174 determines the second liveness data 176.

Returning to 556, if yes the process may proceed to 580.

At 580 the second input image data 112(2) is processed to determine if a hand is detected. In some implementations 580 may be omitted and the process may proceed to 582. If a hand is not detected, the process may proceed to 558. If a hand is detected, the process proceeds to 582.

At 582 second position data 156 is determined.

At 584 a determination is made as to whether the second position data 156 is within a threshold position. In some implementations a different threshold position may be specified, compared to 514. For example, a second threshold position may be used that provides a desired position of the hand 102 in one or more of the first FOV 110(1) or the second FOV 110(2).

If the second position data 156 is deemed to not be within the threshold position, the process may proceed to 558. If the position data 156 is deemed to be within the threshold position, the process may proceed to 586.

At 586 second pose data 158 is determined. The second pose data 158 is indicative of a pose of the portion of the user, such as the hand 102, as depicted in the second input image data 112(2).

At 588 a determination is made as to whether the second pose data 158 is within a threshold pose. In some implementations a different threshold pose may be specified, compared to 518. For example, a second threshold pose may be used that provides a desired pose suitable for processing by the representation network module(s) 420.

At 590 at least a portion of one or more of the first input image data 112(1) or the second input image data 112(2) is determined to be valid biometric input image data 184. For example, as described with regard to FIG. 3, input image data 112 that is acquired within a valid interval 320 may be deemed to be valid biometric input image data 184.

At 592 representation data 436 is determined based on the valid biometric input image data 184. For example, one or more of the images of the first input image data 112(1) or the second input image data 112(2) may be processed by the representation network module(s) 420.

In some implementations other processing may be performed before input image data 112 is processed by the representation network module(s) 420. For example, the valid biometric input image data 184 may be filtered based on one or more characteristics to determine a subset of images. Continuing the example, the subset of images may be images of the valid biometric input image data 184 that satisfy one or more conditions such as sharpness, contrast, and so forth being within threshold values.

In some implementations the order of one or more operations of the process 500 may be changed. For example, the determination and assessment of the pose data 158 may be performed before the determination and assessment of the position data 156.

In some implementations, a single previously trained machine learning system may accept the input image data 112 and determine as output a determination one or more of whether a hand is detected, the position data 156, or the pose data 158.

FIG. 6 is a block diagram 600 of the input device 104, according to some implementations.

One or more power supplies 602 are configured to provide electrical power suitable for operating the components in the input device 104. In some implementations, the power supply 602 may comprise an external power supply that is supplied by line voltage, rechargeable battery, photovoltaic cell, power conditioning circuitry, wireless power receiver, and so forth.

The input device 104 may include one or more hardware processors 604 (processors) configured to execute one or more stored instructions. The processors 604 may comprise one or more cores. One or more clocks 606 may provide information indicative of date, time, ticks, and so forth. For example, the processor 604 may use data from the clock 606 to generate a timestamp, trigger a preprogrammed action, and so forth.

The input device 104 may include one or more communication interfaces 608 such as input/output (I/O) interfaces 610, network interfaces 612, and so forth. The communication interfaces 608 enable the input device 104, or components thereof, to communicate with other devices or components. The communication interfaces 608 may include one or more I/O interfaces 610. The I/O interfaces 610 may comprise interfaces such as Bluetooth, ZigBee, Inter-Integrated Circuit (I2C), Serial Peripheral Interface bus (SPI), Universal Serial Bus (USB) as promulgated by the USB Implementers Forum, RS-232, and so forth.

The network interfaces 612 are configured to provide communications between the input device 104 and other devices, such as access points, point-of-sale devices, payment terminals, servers, and so forth. The network interfaces 612 may include devices configured to couple to wired or wireless personal area networks (PANs), local area networks (LANs), wide area networks (WANs), and so forth. For example, the network interfaces 612 may include devices compatible with Ethernet, Wi-Fi, 5G, 6G, LTE, and so forth.

The input device 104 may also include one or more buses or other internal communications hardware or software that allow for the transfer of data between the various modules and components of the input device 104. For example, the input device 104 may use one or more Universal Serial Bus interfaces.

The input device 104 may include tamper detection circuitry 660. In one implementation, the tamper detection circuitry 660 may comprise a trusted platform module (TPM). The TPM may comprise a dedicated processor that is also powered independently of the power supply 602. For example, the TPM may be powered by a battery. The tamper detection circuitry 660 may be connected to, or receive information about the status of, one or more tamper detection devices. For example, the tamper detection circuitry 660 may be connected to a tamper mesh, one or more tamper detection switches, and so forth. If the tamper detection circuitry 660 detects a tamper event, mitigating actions including, but not limited to memory erasure, self-destruction, and so forth may be performed. For example, if the tamper detection circuitry 660 detects a break in a tamper detection cover, the cryptographic keys stored within the memory 620 may be erased.

The tamper detection circuitry 660 may store data indicative of an order of occurrence of a plurality of tamper events. For example, a first change indicative of the tamper mesh being broken at a first time may be determined. Continuing the example, a second change indicative of the tamper mesh being broken at a second time after the first time may then be determined. The tamper detection circuitry 660 may store data indicative of the order of occurrence, indicating that the first change occurred before the second change. In some implementations, mitigating actions may be determined based on the order of occurrence. For example, a first order of occurrences of tamper events may result in a first action, while a second order of occurrences of tamper events may result in a second action.

The I/O interface(s) 610 may couple to one or more I/O devices 614. The I/O devices 614 may include input devices 616 and output devices 618.

The input devices 616 may include one or more of the visible light camera 108(1), the IR camera 108(2), the distance sensor 144, or the spectroscopy sensor 170. Other input devices 616 may include one or more of a card reader 616(1), a switch 616(2), a touch sensor 616(3), a microphone 616(4), and so forth.

Other distance sensors 144 may be employed by the input device 104. For example, a second distance sensor 144 may be positioned on the input device 104 to detect the presence of an object outside of the first FOV 110(1). For example, the second distance sensor 144 may be arranged to detect a user as they approach the input device 104. Responsive to this detection, the input device 104 may present information on the display 650, operate the visible light sources 140, operate the IR light sources 142, operate the cameras 108, and so forth.

The card reader 616(1) may comprise a smart card reader that provides wired or wireless communication with a smart card such as an EMV card. For example, the user may insert an EMV card which, along with the valid biometric input image data 182, is used to authorize a transaction. In another example, the card reader 616(1) may comprise a contactless card reader that acquires information from corresponding circuitry with a smartphone, fob, or other device.

The switch 616(2) is configured to accept input from the user. The switch 616(2) may comprise mechanical, capacitive, optical, or other mechanisms. For example, the switch 616(2) may comprise mechanical switches configured to accept an applied force from a user's finger press to generate an input signal.

The touch sensor 616(3) may use resistive, capacitive, surface capacitance, projected capacitance, mutual capacitance, optical, Interpolating Force-Sensitive Resistance (IFSR), or other mechanisms to determine the position of a touch or near-touch of the user. For example, the IFSR may comprise a material configured to change electrical resistance responsive to an applied force. The location within the material of that change in electrical resistance may indicate the position of the touch. For example, the touch sensor 616(3) may be integrated with the display 650 to provide a touchscreen.

The microphone 616(4) may be configured to acquire information about sound present in the environment. In some implementations, a plurality of microphones 616(4) may be used to form a microphone array. The microphone array may implement beamforming techniques to provide for directionality of gain. For example, the gain may be directed towards the expected location of the user during operation of the input device 104.

The output devices 618 may include one or more of the visible light sources 140, the IR light source 142, the display 650, a speaker 652, printer, haptic output device, or other devices. For example, the display 650 may be used to provide information via a graphical user interface to the user. In another example, a printer may be used to print a receipt.

In some embodiments, the I/O devices 614 may be physically incorporated with the input device 104 or may be externally placed.

The input device 104 may include one or more memories 620. The memory 620 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 620 provides storage of computer-readable instructions, data structures, program modules, and other data for the operation of the input device 104. A few example functional modules are shown stored in the memory 620, although the same functionality may alternatively be implemented in hardware, firmware, or as a system on a chip (SOC).

The memory 620 may include at least one operating system (OS) module 622. The OS module 622 is configured to manage hardware resource devices such as the I/O interfaces 610, the network interfaces 612, the I/O devices 614, and provide various services to applications or modules executing on the processors 604. The OS module 622 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Washington, USA; the Android operating system from Google Corporation of Mountain View, California, USA; the iOS operating system from Apple Corporation of Cupertino, California, USA; or other operating systems.

A data store 624 may be stored in the memory 620 as well as the following modules. These modules may be executed as foreground applications, background tasks, daemons, and so forth. The modules may include one or more of a communication module 626, the liveness trigger module 148, the image analysis module 150, the device control module 162, the the MWRS analysis module 174, the validity module 180, representation network module(s) 420, or other modules 630. The data store 624 may use a flat file, database, linked list, tree, executable code, script, or other data structure to store information. In some implementations, the data store 624 or a portion of the data store 624 may be distributed across one or more other devices.

A communication module 626 may be configured to establish communications with one or more other devices. The communications may be authenticated, encrypted, and so forth. The communication module 626 may also control the communication interfaces 608.

The device control module 162 is configured to operate one or more of the devices of the input device 104. During operation, the device control module 162 may send control instructions 164 to one or more devices of the input device 104. One or more operating parameters 632 may be stored in the memory 620. The operating parameters 632 may specify operation of the device control module 162, such as data sample rate, sample frequency, scheduling, and so forth. The device control module 162 may be configured to operate the input devices 616, output devices 618, and so forth. For example, the device control module 162 may operate one or more of the input devices 616 to determine sensor data 634. In another example, responsive to receipt of a liveness trigger 160, the device control module 162 may operate the multiwavelength light sources 232 and the spectroscopy sensor 170 to determine intensity data 172 and subsequently liveness data 176.

The sensor data 634 may be sent to another device, processed by the processor 604, and so forth. For example, the sensor data 634 such as valid biometric input image data 182 may be processed by the representation network module (s) 420 to determine representation data 436. The representation data 436 may be encrypted and sent to an external device, such as a server. In the event of a tamper event detected by the tamper detection circuitry 660, the sensor data 634 may be erased.

The device control module 162 may obtain data from other input devices 616. For example, card data 636 may be obtained from the card reader 616(1). The card data 636 may comprise encrypted data provided by a processor of the card reader 616(1). In the event of a tamper event detected by the tamper detection circuitry 660, the card data 636 may be erased.

Device identification data 638 may be stored in the data store 624. The device identification data 638 may provide information that is indicative of the specific input device 104. For example, the device identification data 638 may comprise a cryptographically signed digital signature. In the event of a tamper event detected by the tamper detection circuitry 660, this digital signature may be erased.

The device control module 162 may store input data 642 obtained from other sensors. For example, input from a switch 616(2) or touch sensor 616(3) may be used to generate input data 642.

The data store 624 may store output data 644. For example, the output data 644 may comprise images to be presented on the display 650.

The other modules 630 may include a user interface module that provides a user interface using one or more of the I/O devices 614. The user interface module may be used to obtain input from the user, present information to the user, and so forth. For example, the user interface module may accept input from the user via the touch sensor 616(3) and use the visible light source(s) 140 to provide output to the user. For example, the user interface module may provide user guidance to direct the user to place their hand 102 in a desired position and pose. Continuing the example, the user interface module may operate the visible light sources 140, present output on the display 650, emit sound from the speaker 652, and so forth to direct the user to place their hand in a desired position and pose relative to the input device 104.

Other data 646 may also be stored in the data store 624.

The devices and techniques described in this disclosure may be used in a variety of settings. For example, the system may be used in conjunction with a point-of-sale (POS) device. The user may present their hand 102 to an input device 104 that is used to obtain biometric data indicative of intent and authorization to pay with an account associated with their identity. In another example, a robot may incorporate an input device 104. The robot may use the input device 104 to obtain valid biometric input image data 182 that is then used to determine whether to deliver a parcel to the user, and based on the identification, which parcel to deliver.

The processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A device comprising:
a first camera having a first field of view (FOV);
one or more light sources to illuminate at least a portion of the first FOV;
a spectroscopy sensor having a second FOV, wherein the second FOV overlaps at least a portion of the first FOV;
a memory, storing first computer-executable instructions; and
a hardware processor to execute the first computer-executable instructions to:
operate the one or more light sources to emit a first set of wavelengths;
acquire, using the first camera, first input image data at a first time;
determine, based on the first input image data, first position data indicative of a position of a hand of a user depicted within the first input image data;
determine that the first position data is indicative of the hand of the user being within a first threshold position;
determine, based on the first input image data, first pose data indicative of a pose of the hand of the user depicted within the first input image data;
determine that the first pose data is indicative of the hand of the user having a pose that is within a first threshold pose;
responsive to the determination that the first position data is indicative of the hand of the user being within the first threshold position and the determination that the first pose data is indicative of the hand of the user having a pose that is within the first threshold pose, determine that quality of the hand depicted within the first input image data is acceptable;
responsive to the determination that the quality of the hand depicted within the first input image data is acceptable for use:
operate the one or more light sources to emit a second set of wavelengths,
operate the spectroscopy sensor at a second time to determine a first set of intensity data indicative of intensity of light for a plurality of wavelengths, and
determine, based on the first set of intensity data, a first value indicative of liveness of the hand; and
responsive to the determination that the first value is indicative of liveness of the hand:
acquire, using the first camera, second input image data at a third time; and
perform, based on the second input image data, one or more of:
a continuity check, or
a validity check.

2. The device of claim 1, further comprising:
a distance sensor; and
the hardware processor to further execute the first computer-executable instructions to:
determine, using the distance sensor, first distance data; and
determine that the first distance data is indicative of presence of the hand within a threshold distance.

3. The device of claim 1, further comprising:
a communication interface; and
the hardware processor to further execute the first computer-executable instructions to:
determine that the first time and the second time are within a first time interval;
determine representation data based on one or more of the first input image data or the second input image data; and
send the representation data using the communication interface.

4. The device of claim 1, the hardware processor to further execute the first computer-executable instructions to:
determine, based on the second input image data, second position data indicative of a position of the hand of the user depicted within the second input image data;
determine that the second position data is indicative of the hand of the user being within a second threshold position;
determine, based on the second input image data, second pose data indicative of a pose of the hand of the user depicted within the second input image data;
determine that the second pose data is indicative of the hand of the user having a second pose that is within a second threshold pose;
determine that the third time and the second time are within a first time interval; and
determine representation data based on the second input image data.

5. The device of claim 1, wherein the first camera is responsive to visible light; and
the device further comprising:
a second camera having a third FOV, wherein the second camera is responsive to infrared light; and
the hardware processor to further execute the first computer-executable instructions to:
operate the one or more light sources to emit a third set of wavelengths that comprise infrared light;
acquire, using the second camera, third input image data at a fourth time;
determine, based on the third input image data, second position data indicative of a second position of the hand of the user depicted within the third input image data;
determine that the second position data is indicative of the hand of the user being within a second threshold position;
determine, based on the third input image data, second pose data indicative of a second pose of the hand of the user depicted within the third input image data;
determine that the second pose data is indicative of the hand of the user having a second pose that is within a second threshold pose;
determine that the fourth time and the second time are within a first time interval; and
determine representation data based on the third input image data.

6. The device of claim 1, the hardware processor to further execute the first computer-executable instructions to:
operate the one or more light sources to emit the second set of wavelengths at the second time as a sequence such that a first wavelength is emitted at a fourth time and a second wavelength is emitted at a fifth time; and operate the spectroscopy sensor to determine first intensity data at the fourth time and second intensity data at the fifth time, wherein the first set of intensity data comprises the first intensity data and the second intensity data; and wherein the spectroscopy sensor comprises a photodetector.

7. The device of claim 1, the hardware processor to further execute the first computer-executable instructions to:

operate the one or more light sources to emit the second set of wavelengths such that a first wavelength and a second wavelength are emitted at the second time; and wherein the spectroscopy sensor comprises a first detector portion that is sensitive to the first wavelength and a second detector portion that is sensitive to the second wavelength.

8. A method comprising:

operating one or more light sources to emit a first set of wavelengths;

acquiring, using a first camera having a first field of view (FOV), a first set of input images during a first time interval, wherein the first set of input images depict a hand of a user;

determining, based on the first set of input images, first characteristic data associated with the hand;

determining that the first characteristic data is within a specified threshold range;

based on the determining that the first characteristic data is within the specified threshold range, determining that a quality of the hand as depicted within the first set of input images is acceptable;

responsive to the determining that the quality of the hand as depicted within the first set of input images is acceptable:

operating the one or more light sources to emit a second set of wavelengths, operating a first sensor during a second time interval to determine a first set of intensity data indicative of intensity of light for a plurality of wavelengths, and determining, based on the first set of intensity data, a first value that is indicative of liveness of the hand; and responsive to the determining that the first value is indicative of liveness of the hand:

acquire a second set of input images during a third time interval, and check for validity of one or more of the first set of images or the second set of images.

9. The method of claim 8, wherein the first characteristic data is indicative of one or more of:

first position data indicative of a position of a hand within the first FOV, or first pose data indicative of a pose of the hand within the first FOV.

10. The method of claim 8, further comprising:

determining a first subset of the first set of input images, wherein for each image of the first subset:

the each image is associated with a respective timestamp, and the respective timestamp is within a fourth time interval of the second time interval; and determining representation data based on the first subset.

11. The method of claim 8, wherein the first camera is responsive to visible light; and the method further comprising:

operating the one or more light sources to emit a third set of wavelengths that comprise infrared light;

acquiring, using a second camera that is responsive to infrared light, a third set of input images during a second-fourth time interval;

determining, based on the third set of input images, second characteristic data;

determining a first subset of the third set of input images, wherein for each image of the first subset of the third set of input images:

the second characteristic data associated with the each image is within the specified threshold range, the each image is associated with a respective timestamp, and the respective timestamp is within a fifth time interval of the second time interval; and determining representation data based on the first subset of the third set of input images.

12. The method of claim 8, wherein the second time interval is within the third time interval, and the method further comprising:

determining representation data based on the second set of input images.

13. The method of claim 8, further comprising:

determining, based on the second set of input images, second characteristic data;

determining that the second characteristic data associated with each image of the second set of images satisfies a specified threshold value; and determining representation data based on the second set of input images.

14. A device comprising:

a first camera having a first field of view (FOV);

one or more light sources to illuminate at least a portion of the first FOV;

a first sensor having a second FOV, wherein the second FOV overlaps at least a portion of the first FOV;

a memory, storing first computer-executable instructions; and a hardware processor to execute the first computer-executable instructions to:

operate the one or more light sources to emit a first set of wavelengths;

acquire, using the first camera, a first set of input images during a first time interval, wherein the first set of input images depicts a hand of a user;

determine, based on the first set of input images, first characteristic data associated with the hand;

determine that the first characteristic data is within a specified threshold range;

based on the determination that the first characteristic data is within the specified threshold range, determine that a quality of the hand as depicted within the first set of input images is acceptable;

responsive to the determination that the quality of the hand as depicted within the first set of input images is acceptable:

operate the one or more light sources to emit a second set of wavelengths, operate the first sensor during a second time interval to determine a first set of intensity data indicative of intensity of light for a plurality of wavelengths, and determine, based on the first set of intensity data, a first value indicative of liveness of the hand.

15. The device of claim 14, wherein the first characteristic data associated with the hand is indicative of one or more of:

first position data indicative of a position of the hand within the first FOV, or first pose data indicative of a pose of the hand within the first FOV.

16. The device of claim 14, further comprising:

a distance sensor; and the hardware processor to further execute the first computer-executable instructions to:

determine, using the distance sensor, first distance data; and determine the first distance data is indicative of presence of the hand within a threshold distance.

17. The device of claim 14, the hardware processor to further execute the first computer-executable instructions to:

determine a first subset of the first set of input images, wherein for each image in the first subset:

the each image is associated with a respective timestamp, and the respective timestamp is within a third time interval of the second time interval; and determine representation data based on the first subset.

18. The device of claim 14, wherein the first camera is responsive to visible light; and the device further comprising:

a second camera having a third FOV, wherein the second camera is responsive to infrared light;

the hardware processor to further execute the first computer-executable instructions to:

operate the one or more light sources to emit a third set of wavelengths that comprise infrared light;

acquire, using the second camera, a third set of input images during a third time interval;

determine, based on the third set of input images, second characteristic data;

determine a first subset of the third set of input images, wherein for each image of the first subset of the third set of input images:

the second characteristic data associated with the each image is within the specified threshold range, the each image is associated with a respective timestamp, and the respective timestamp is within a fourth time interval of the second time interval; and determine representation data based on the first subset.

19. The device of claim 14, the hardware processor to execute the first computer-executable instructions to:

operate the one or more light sources to emit the second set of wavelengths as a sequence such that a first wavelength is emitted during a third time interval and a second wavelength is emitted during a fourth time interval; and operate the first sensor to determine first intensity data during the third time interval and second intensity data during the fourth time interval, wherein the first set of intensity data comprises the first intensity data and the second intensity data; and wherein the first sensor comprises a photodetector.

20. The device of claim 14, the hardware processor to further execute the first computer-executable instructions to:

operate the one or more light sources to emit the second set of wavelengths such that a first wavelength and a second wavelength are emitted at a same time; and wherein the first sensor comprises a first detector portion that is sensitive to the first wavelength and a second detector portion that is sensitive to the second wavelength.

* * * * *